United States Patent
Johnson

(10) Patent No.: US 10,159,889 B2
(45) Date of Patent: Dec. 25, 2018

(54) CONSENSUS-SCORING WRISTBAND FOR PICK-UP BASKETBALL

(71) Applicant: Justin Johnson, Elkridge, MD (US)

(72) Inventor: Justin Johnson, Elkridge, MD (US)

( * ) Notice: Subject to any disclaimer, the term of this patent is extended or adjusted under 35 U.S.C. 154(b) by 33 days.

(21) Appl. No.: 15/239,749

(22) Filed: Aug. 17, 2016

(65) Prior Publication Data

US 2017/0050103 A1    Feb. 23, 2017

Related U.S. Application Data

(60) Provisional application No. 62/205,741, filed on Aug. 17, 2015.

(51) Int. Cl.
*A63B 71/06* (2006.01)
*A63B 24/00* (2006.01)
*A63B 69/00* (2006.01)

(52) U.S. Cl.
CPC ...... *A63B 71/0669* (2013.01); *A63B 24/0062* (2013.01); *A63B 69/0071* (2013.01); *A63B 2071/0663* (2013.01); *A63B 2225/50* (2013.01)

(58) Field of Classification Search
None
See application file for complete search history.

(56) References Cited

U.S. PATENT DOCUMENTS

| | | | |
|---|---|---|---|
| 4,097,855 A * | 6/1978 | Salvo | A63B 71/06 340/323 R |
| 5,039,977 A | 8/1991 | Mele et al. | |
| 5,134,565 A * | 7/1992 | Herbertz | G04G 9/0064 273/DIG. 26 |
| 7,773,461 B1 * | 8/2010 | Crosby, Sr. | A63B 71/0669 368/10 |
| 8,845,461 B2 | 9/2014 | Duke | |
| 2006/0160639 A1 | 7/2006 | Klein | |
| 2012/0256373 A1 * | 10/2012 | Tam | A63D 15/20 273/148 R |
| 2012/0322587 A1 * | 12/2012 | Duke | A63B 69/0071 473/450 |
| 2014/0163990 A1 * | 6/2014 | Street | A63B 71/0622 704/258 |
| 2014/0222177 A1 | 8/2014 | Thurman et al. | |

FOREIGN PATENT DOCUMENTS

| CN | 201454012 U | 5/2010 |
|---|---|---|
| CN | 104248836 U | 12/2014 |

* cited by examiner

*Primary Examiner* — Damon Pierce

(57) ABSTRACT

A consensus-scoring wristband allows the user to track the points scored in a pick-up basketball game. The wristband is similar in structure and function to a sports wristband, but provides a consensus-scoring function. Each user may quickly add points as they are scored to each team's score, such that the score may be easily kept while participating in the game. A mobile application is also provided, enabling the user to transmit and update the score to a smartphone. The application employs consensus-scoring, such that the input from the wristband users may be relied upon as an accurate score for the game.

2 Claims, 2 Drawing Sheets

US 10,159,889 B2

CONSENSUS-SCORING WRISTBAND FOR PICK-UP BASKETBALL

CROSS-REFERENCE TO RELATED APPLICATIONS

This Application claims the benefit of U.S. Provisional Application No. 62/205,741, filed Aug. 17, 2015, which is hereby incorporated by reference.

STATEMENT REGARDING FEDERALLY SPONSORED RESEARCH OR DEVELOPMENT

Not Applicable

PARTIES TO A JOINT RESEARCH AGREEMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The invention relates generally to athletic equipment and in particular to a scorekeeping wristband. Sports wristbands such as Fitbit® are growing rapidly in popularity. These are powered by rechargeable batteries like smartphones, but provide various types of support for athletic activities such as providing stopwatch and pedometer functions, tracking the wearer's pulse rate, and serving as a conventional digital watch. Unfortunately, the designers of sports wristbands have overlooked the need to keep score in team sports, such as a pick-up basketball game. Such informal games rarely have referees or any support staff, so players must keep score; but the intensely competitive nature of many pick-up games demands accurate, reliable scorekeeping.

A search of the prior art reveals various scoring systems which have been developed. None are closely related to the present invention, but several include features which resemble those of the present invention. Each has proven to be less than satisfactory in its own way.

Hoop tracker, U.S. Pat. No. 8,845,461 (priority Sep. 1, 2010), provides a wireless shot tracking system for basketball games and practice sessions, including a programmable electronic unit that is in electrical communication with a shot detector for automatically tracking and displaying real-time shooting percentages of basketball players during basketball shooting sessions. The tracking system further provides a telescoping pole for mounting the shot detector to a basketball rim from the ground. The programmable electronic unit provides a program mode, a play mode, a review mode and a random mode to help improve the shooting skills of a basketball player from different shooting locations on a basketball court. The shot detector includes one or more vibration sensors to detect missed shots, and an activator that extends along a horizontal axis in a central region of the basketball hoop to detect made shots. The programmable electronic unit interfaces with a computer via a USB port for uploading or downloading program updates or shooting session data.

Basketball sensing apparatus, U.S. Patent App. Pub. No. US2014/0222177 (priority Nov. 9, 2012), provides an apparatus including a non-transitory computer-readable medium to direct a processor to: receive signals indicating a made basketball shot or a missed basketball shot of a basketball by a person during a basketball shooting session, receive signals indicating a location from which each made basketball shot is made, and determine and output a user cumulative score for the person for the basketball shooting session, the cumulative score being based upon the location of each made basketball shot.

Real-time wireless sensor scoring, U.S. Patent App. Pub. No. US2006/0160639 (priority Jan. 14, 2005), provides mechanisms and methods for measuring basketball shooting performance. These mechanisms and methods for measuring shooting performance make it possible for coaches and players to obtain information they need to measure levels of play, improve and maintain skills, select players to meet game situations and team requirements, and make decisions on player roles.

Multifunctional basketball game monitoring unit, U.S. Pat. No. 5,039,977 (priority Jan. 5, 1989) provides a basketball game monitoring unit capable of sensing shots attempted and shots made in normal play, and shots attempted and shots made from a spot location, and further adjusting the score for the time a player remains in the air when shooting from the spot location; the unit acting to calculate, store, and display total time in play, total score, total percent of baskets made of total baskets attempted and total score shooting from the spot location for each of two backboard hoop assemblies.

Electronic score indicator, Chinese Patent No. CN201454012 (filed Apr. 22, 2009), provides an electronic score indicator, which comprises a transmitter device and a receiver device. Wireless communication modules are arranged in the transmitter device and the receiver device. The wireless communication module in the transmitter device is connected with the wireless communication module in the receiver device in a signaling way. The utility model has the advantages that the installation is simple and the carrying is convenient.

Intelligent basketball scoring system, Chinese Patent No. CN104248836 (filed Jun. 29, 2013), provides an intelligent basketball scoring system, which comprises a central processing unit, an electronic scoring plate, a plurality of cameras and an optical sensing sensor, wherein the cameras are arranged around a court, the optical sensing sensor is arranged on a basket, a microprocessor is arranged in the central processing unit, and the electronic scoring plate, the cameras and the optical sensing sensor are all electrically connected with the microprocessor. The intelligent basketball scoring system has the advantages that a 3D (three-dimensional) simulation dynamic model can be built in the microprocessor arranged in the central control device according to the collected multi-angle video information, sportsmen and a basketball on the court are shown in the 3D simulation dynamic model like 3D games, the goal state is determined according to the optical sensing sensor arranged on the basket, in addition, the goal scores are accurately determined according to the 3D simulation dynamic model, the intelligence degree is high, and the score judgment is accurate, so a referee can pay more attention to the illegality conditions on the court, and the competition fairness is improved.

Prior art inventions generally provide some sort of electronic scoring system for a basketball game or shooting session, but the components of the system are not portable and represent a substantial monetary investment. The present invention has been developed for the purpose of addressing and resolving the disadvantages of the prior art inventions. A scorekeeping wristband, which enables the user to keep score while playing the game and transmits the scoring to a smartphone application, would resolve this problem.

In addition to the prior art inventions mentioned above, there are also a few prior art inventions similar to the present invention in respect that they are also electronic scoring devices. These include: Electronic scoring device for tennis competitions, U.S. Pat. No. 5,134,565 (priority Dec. 21, 1990), Electronic tennis scoring system, U.S. Pat. No. 4,097,855 (priority Nov. 25, 1977), and Tennis umpire, U.S. 20140163990 (priority Dec. 7, 2012). These inventions however, are intended to provide a type of electronic scoring system for participants playing within the game of tennis. A key distinction between the present invention and the prior art inventions is demonstrated in their abilities to record and display points within their respective games. The game of tennis is played at a more interval-based pace; after a point is scored, whether scored from the results of a fast-paced rally or scored immediately from a powerful serve without a rally, there is always an allotted time period of rest that follows before the next serve in to play. The prior art inventions mentioned above thus enable the user to input the score of the game either auditorily, or manually by pressing a scoring button during this routine break in gameplay. The prior art inventions however, fail to disclose the necessary methods of recording game scores in real-time during a fast-paced game such as pick-up basketball. The present invention has been developed to address this issue with consensus-scoring, which enables the consensus-scoring wristband users to display inputted scores to rely upon an accurate score during gameplay.

SUMMARY OF THE INVENTION

Accordingly, the invention is directed to a consensus-scoring wristband. The wristband is similar in structure and function to a sports wristband, but provides a scorekeeping function for pick-up basketball games. Each user may quickly add points as they are scored to each team's score, such that the score may be easily kept while participating in the game. A mobile application is also provided, enabling the user to transmit and update the score to a smartphone. The application employs consensus-scoring, such that the input from the wristband users may be relied upon as an accurate score for the game FIG. 3.

Additional features and advantages of the invention will be set forth in the description which follows, and will be apparent from the description, or may be learned by practice of the invention. The foregoing general description and the following detailed description are exemplary and explanatory and are intended to provide further explanation of the invention.

BRIEF DESCRIPTION OF THE DRAWINGS

The accompanying drawings are included to provide a further understanding of the invention and are incorporated into and constitute a part of the specification. They illustrate one embodiment of the invention and, together with the description, serve to explain the principles of the invention.

DETAILED DESCRIPTION OF THE INVENTION

Referring now to the invention in more detail, the invention is directed to a scorekeeping wristband 10.

The embodiment is comprised of a wristband 10 (which may include flexible band 14 and a socket 35 on a surface of the wristband for a removable recharging cord), which is similar in structure and function to a conventional sports wristband such as the Fitbit® Flex™, but provides a consensus-scoring function for pick-up basketball games.

Figure 1:
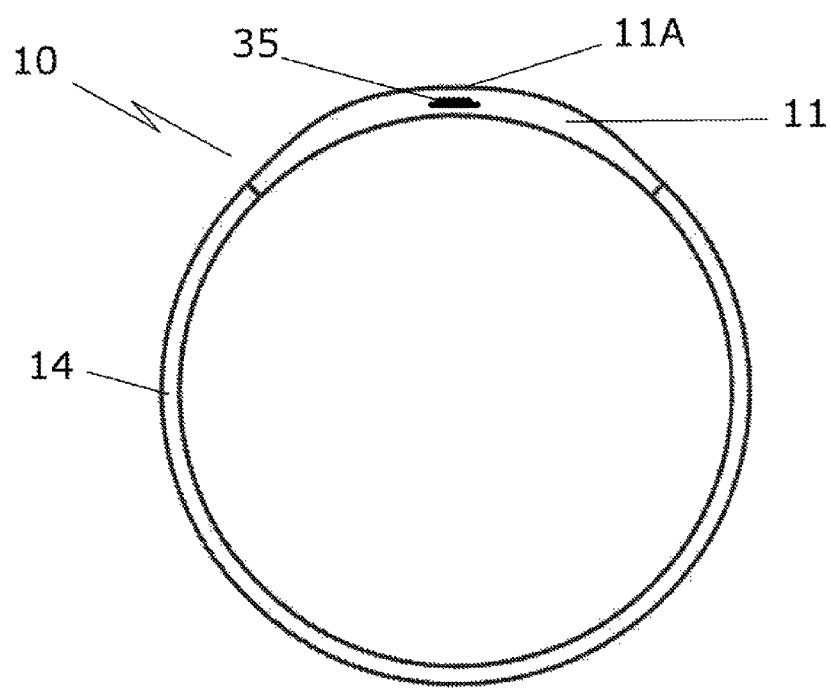
FIG. 1 is a side view of the embodiment, displaying the wristband, the information processing smart object, and a surface of the body with a socket for a removable recharging cord.
Figure 2:
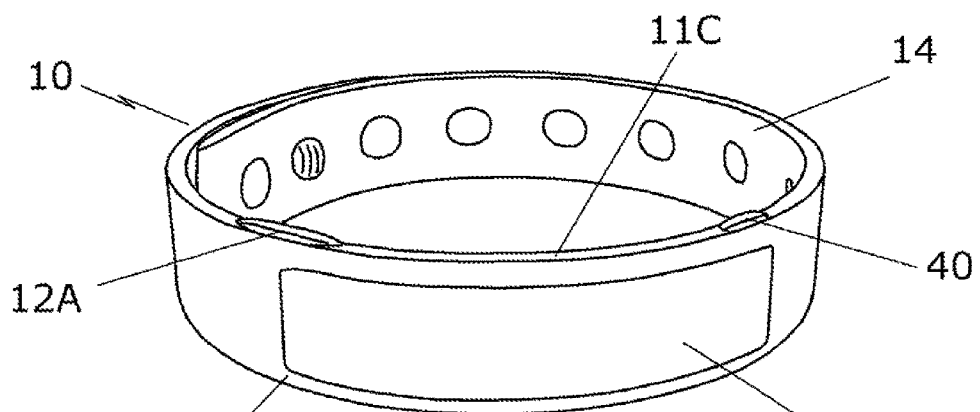
FIG. 2 is a front view of the embodiment, displaying the wristband, the information processing smart object, the scoring button, the digital scoring display, and the power button.
Figure 3:
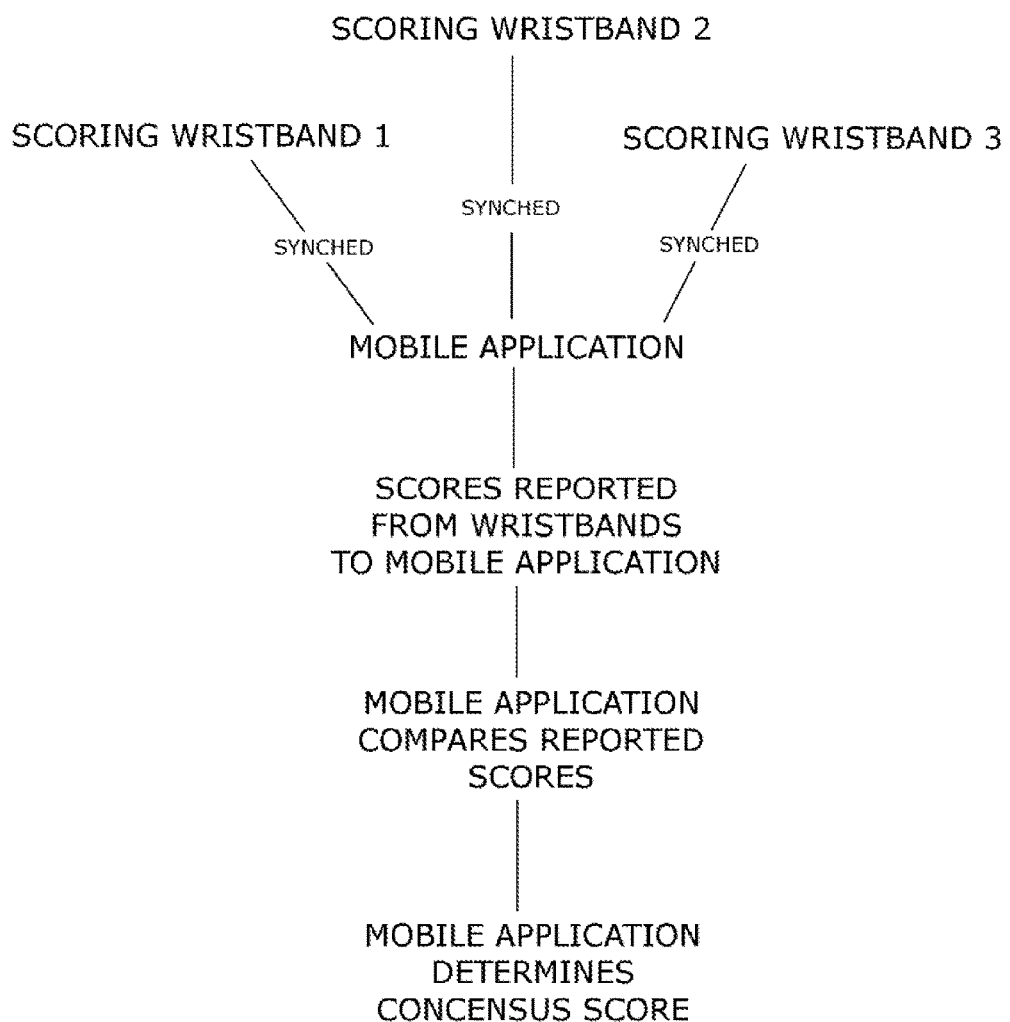
FIG. 3 is a flow chart of the wristband system.

The speed of play inherent in basketball games may introduce the possibility of an inaccurate score whenever a single user serves as the scorekeeper. Thus users of the wristband 10 are enabled to keep score in each game. The application employs consensus-scoring, such that the input from each user of the wristband 10 participating in the game may be relied upon as an accurate score for the game. Each point scored by a user is recorded as part of the official score. The entered score is then compared by the application (FIG. 3), to accurately determine which team username and player scored the point. The official score is then displayed on all wristbands participating in the game.

The wristband 10 provides a scoring button 12A. The scoring button 12A is located on the top edge 11C of the information processing smart object 11. A power button 40 is also provided on the top edge 11C of the information processing smart object 11. The embodiment provides a digital scoring display 13. The digital scoring display 13 shows the score and the username of the team and player.

When users synchronize their wristbands 10 to the mobile application they are assigned usernames as well as teams. The scoring player then presses the scoring button 12A on their wristband 10. Each wristband is associated with a synchronized team and player username and the point is distributed accordingly with the consensus-scoring function FIG. 3. The digital scoring display 13 then adds the point to the appropriate team and the proper score is displayed on all player's wristbands 10.

While the foregoing written description of the invention enables one of ordinary skill to make and use what is presently considered to be the best mode thereof, those of ordinary skill in the art will understand and appreciate the existence of variations, combinations, and equivalents of the specific embodiment, method, and examples herein. The invention should, therefore, not be limited by the above described embodiment, method, and examples, but by all embodiments and methods within the scope and spirit of the invention.

I claim:

1. A consensus-scoring wristband for pick-up basketball, comprising:
   an information processing smart object;
   said informational processing smart object providing a digital scoring display to display inputted scores from each synchronized team and player username;
   said synchronized team and player username of said digital scoring display enable a user of said consensus-scoring wristband for pick-up basketball to display a team and player username next to said team's score;

a scoring button being configured to enable the user of said consensus-scoring wristband for pick-up basketball participating in a game to press the scoring button to input an addition or deduction of each point scored during gameplay to the score of said team and player username when pressed;

a consensus-scoring function;

said consensus-scoring function enables the user of said consensus-scoring wristband for pick-up basketball to enter each point scored during gameplay which is then compared with each said synchronized team and player username to accurately determine which team username and player scored the point; an official score is then displayed on one or more synchronized consensus-scoring wristbands participating in the game; and a power button configured to activate said consensus-scoring wristband for pick-up basketball and compare and determine scores of said consensus-scoring wristband for pick-up basketball with a smartphone mobile application and the one or more synchronized consensus-scoring wristbands for pick-up basketball when said scores are inputted by said users.

2. The consensus-scoring wristband for pick-up basketball of claim 1, wherein said scoring button is held down shall deduct an allotted number of points from said synchronized team and player username score of one or more said synchronized consensus-scoring wristbands for pick-up basketball with said consensus-scoring function to enable paid user to rely upon an accurate score of the game.

* * * * *